(12) United States Patent
Raver et al.

(10) Patent No.: US 10,420,854 B2
(45) Date of Patent: Sep. 24, 2019

(54) MEDICATED DIAPERS AND METHODS OF MANUFACTURING THEREOF

(71) Applicants: Kristin Raver, Aurora, MN (US); Tracy Harkins-Ripple, Crown Point, IN (US)

(72) Inventors: Kristin Raver, Aurora, MN (US); Tracy Harkins-Ripple, Crown Point, IN (US)

( * ) Notice: Subject to any disclaimer, the term of this patent is extended or adjusted under 35 U.S.C. 154(b) by 916 days.

(21) Appl. No.: 14/965,134

(22) Filed: Dec. 10, 2015

(65) Prior Publication Data

US 2016/0184473 A1    Jun. 30, 2016

Related U.S. Application Data

(60) Provisional application No. 62/090,480, filed on Dec. 11, 2014.

(51) Int. Cl.
*A61F 13/15* (2006.01)
*A61L 15/44* (2006.01)
*A61F 13/49* (2006.01)
*A61F 13/84* (2006.01)

(52) U.S. Cl.
CPC .............. *A61L 15/44* (2013.01); *A61F 13/49* (2013.01); *A61F 13/8405* (2013.01); *A61F 13/15577* (2013.01)

(58) Field of Classification Search
CPC ...... A61L 15/44; A61F 13/49; A61F 13/8405; A61F 13/15577

USPC .......................................... 604/359, 360, 364
See application file for complete search history.

(56) References Cited

U.S. PATENT DOCUMENTS

| | | | | |
|---|---|---|---|---|
| 3,875,942 | A * | 4/1975 | Roberts | A61F 13/512 604/370 |
| 4,221,221 | A * | 9/1980 | Ehrlich | A61F 13/84 206/581 |
| 4,623,339 | A * | 11/1986 | Ciraldo | A61F 13/84 604/359 |
| 4,790,836 | A * | 12/1988 | Brecher | A61F 13/15211 604/359 |
| 6,712,801 | B1 * | 3/2004 | Richardson | A61F 13/49 604/359 |
| 2004/0127866 | A1 * | 7/2004 | Odorzynski | A61F 13/5511 604/359 |
| 2012/0078211 | A1 * | 3/2012 | Akinsanya | A61L 15/44 604/385.06 |
| 2016/0030249 | A1 * | 2/2016 | Caneppele | A61F 13/0253 604/368 |

* cited by examiner

*Primary Examiner* — Jacqueline F Stephens
(74) *Attorney, Agent, or Firm* — Hartman Global IP Law; Gary M. Hartman; Domenica N. S. Hartman

(57) ABSTRACT

A diaper and a method of manufacturing thereof that include a composition located on, in, or near an area of the diaper that will contact skin of an individual when the individual is wearing the diaper. The composition is formulated to reduce the risk of formation of a rash or pressure ulcer on the skin of the individual.

9 Claims, 3 Drawing Sheets

MEDICATED DIAPERS AND METHODS OF MANUFACTURING THEREOF

CROSS REFERENCE TO RELATED APPLICATIONS

This application claims the benefit of U.S. Provisional Application No. 62/090,480, filed Dec. 11, 2014, the contents of which are incorporated herein by reference.

BACKGROUND OF THE INVENTION

The present invention generally relates to diapers. The invention particularly relates to diapers suitable for preventing or reducing the risk of skin rashes and/or pressure sores.

Diapers are commonly worn by infants and children as well as adults with incontinence to prevent leakage of urine or fecal matter. Extended use of diapers may lead to skin rashes that can often be attributed to skin disorders and/or irritants. For example, extended contact between an individual's skin and moisture within the diaper can cause irritation of the outer layer of skin, eventually causing the development of a skin rash if left unaddressed. Furthermore, children and adults that are bedridden and wheelchair-confined are at greater risk for developing pressure (decubitus) ulcers, commonly known as bedsores or pressure sores, which can result from prolonged pressure from an individual's body weight upon bony prominences or other potential pressure points.

In addition to discomfort caused by skin rashes and pressure ulcers, once the outer layer of skin has been damaged, the skin is more vulnerable to secondary infections by bacteria and fungi. Consequently, it is desirable to prevent or reduce the likelihood of the formation of such skin rashes and pressure ulcers to promote the health of the individual. Although there are may types of diapers commercially available, it is believed that all available diapers may cause or promote skin rashes, and that none provide adequate means for reducing or eliminating the risk of skin rashes or the formation of pressure ulcers.

Conventional attempts to prevent skin rash and pressure ulcer formation have included applying some type of medication, for example, a cream, lotion, ointment, powder, etc., to the interior lining of a diaper or directly to the wearer's skin prior to wear. If the individuals' outer layer of skin is prevented from starting to blanch and breakdown, the formation of these skin rashes and pressure ulcers may be at least delayed. However, these practices require the medication to be applied by the individual or a caregiver at every diaper change. In addition, it may be difficult to control the amount of medication applied at each individual application, resulting in waste if excess is applied and resulting in an increased likelihood of skin rash formation if an inadequate amount is applied.

In view of the above, there is an ongoing desire for products and/or methods for decreasing the risk of skin rashes and/or pressure ulcers on individuals that require extended use of diapers, particularly if such products and/or methods were capable of at least partly reducing or preventing the formation of skin rashes and/or pressure ulcers without the need to apply medications prior to securing the diapers to the individuals.

BRIEF DESCRIPTION OF THE INVENTION

The present invention provides pull-ups and diapers (hereinafter, collectively referred to as diapers) suitable for at least partly reducing or preventing the formation of skin rashes and/or pressure ulcers on the skin of individuals prone thereto as a result of extended wearing of diapers or long periods of sitting or lying in a manner that applies pressure to bony prominences or other potential pressure points. The diapers and methods of use thereof preferably do not require medications to be directly applied to the skin of the individual prior to securing the diaper to the individual. The present invention also provides methods of manufacturing such a diaper.

According to one aspect of the invention, a diaper includes a composition located on, in, or near an area of the diaper that will contact skin of an individual when the individual is wearing the diaper. The composition is formulated to reduce the risk of formation of a rash or pressure ulcer on the skin of the individual.

According to another aspect of the invention, a method is provided for manufacturing a diaper adapted to prevent or reduce the risk of forming a rash on skin of an individual due to the individual wearing the diaper or a pressure ulcer on the skin of the individual due to extended periods of applying pressure to the individual's skin. The method includes applying a composition to an area of the diaper that will contact the skin of the individual when the individual is wearing the diaper. The composition is applied prior to the individual wearing the diaper. The method includes concealing the area with a removable cover suitable for preventing loss of the composition prior to donning the diaper. The cover is configured to be removed prior to the individual wearing the diaper. The diaper is then made available for purchase.

A technical effect of the diapers is the ability to provide constant protection to an individual's skin during use of a diaper without the need to apply a medication, for example, a cream, lotion, ointment, powder, etc., to the individual's skin prior to use of the diaper. In particular, it is believed that, by providing the composition on an area of the diaper that will contact the individual's skin during use, the formation of skin rashes and/or pressure ulcers can be significantly reduced or eliminated.

Other aspects and advantages of this invention will be better appreciated from the following detailed description.

DETAILED DESCRIPTION OF THE INVENTION

The present invention is generally applicable to diapers especially of types suitable for extended wear by individuals. Diapers in accordance with aspects of the invention as described hereinafter are configured to reduce or eliminate the risk of skin rashes due to extended use and/or eliminate the risk of pressure ulcers due to extended periods of sitting or lying down. FIGS. 1A, 1B, 2, and 3 represent a medicated diaper 10 in accordance with aspects of the present invention. The diaper 10 may have any shape, size, type, or structure known in the art for use by children, adults, animals, etc. Similar to existing diapers, the medicated diaper 10 depicted in FIGS. 1A, 1B, 2, and 3 is represented as including an absorption area 14 suitable for absorbing urine and/or other liquids and means 18 for securing the diaper 10 to the wearer, for example, tape, hook-and-loop (Velcro®), etc. In addition, the diaper 10 is represented as having an hourglass shape, and as such includes flaps 16 on which the securing means 18 are disposed. Such structures and other additional features common to diapers are well known and therefore will not be discussed further herein. Furthermore, the diaper 10 may be formed of any material or combination of materials, such as those common to diapers known in the art, and preferably provides absorption and leakage prevention properties common for conventional diapers known in the art.

Figure 1:
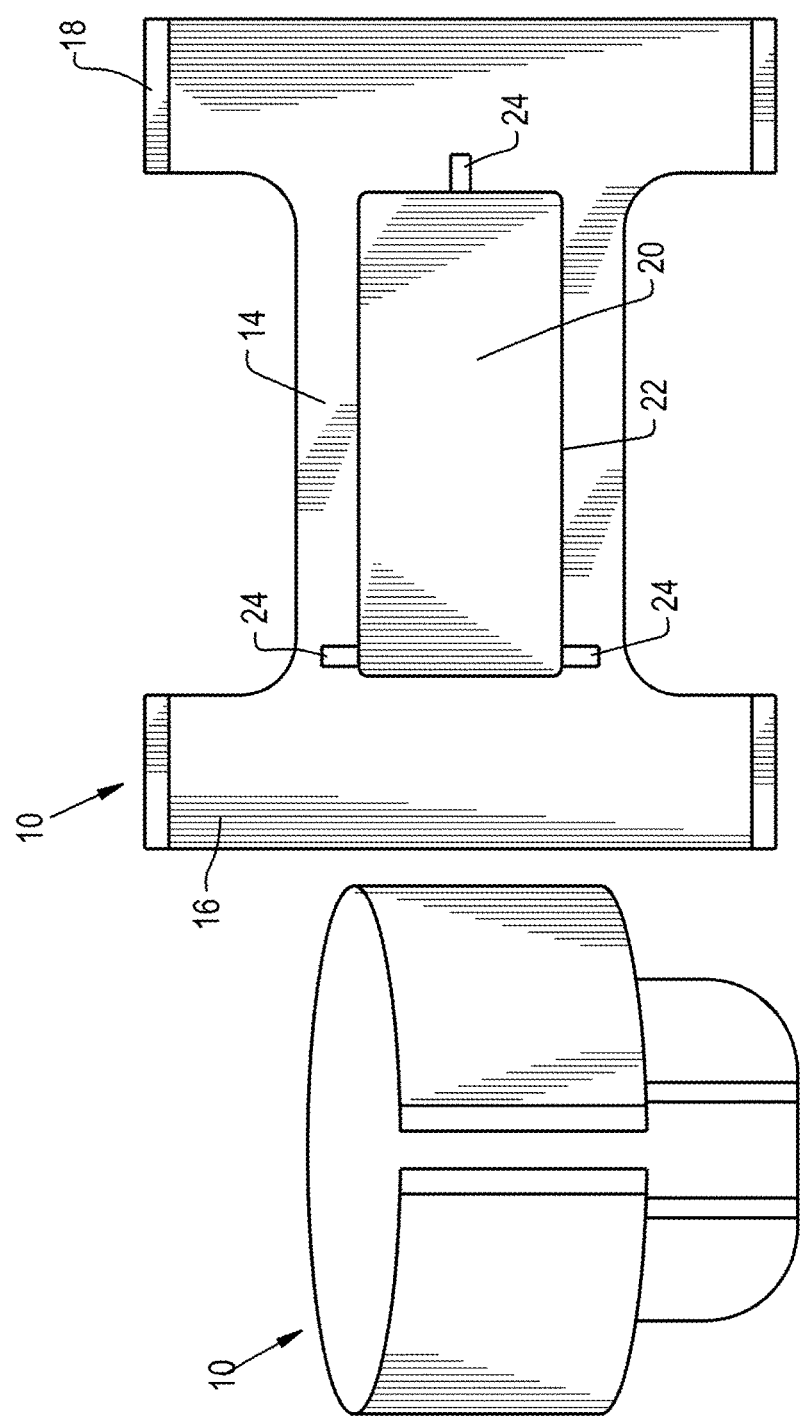
FIGS. 1A and 1B represent, respectively, a closed side view and an open top view of a medicated diaper in accordance with certain aspects of this invention.
Figure 2:
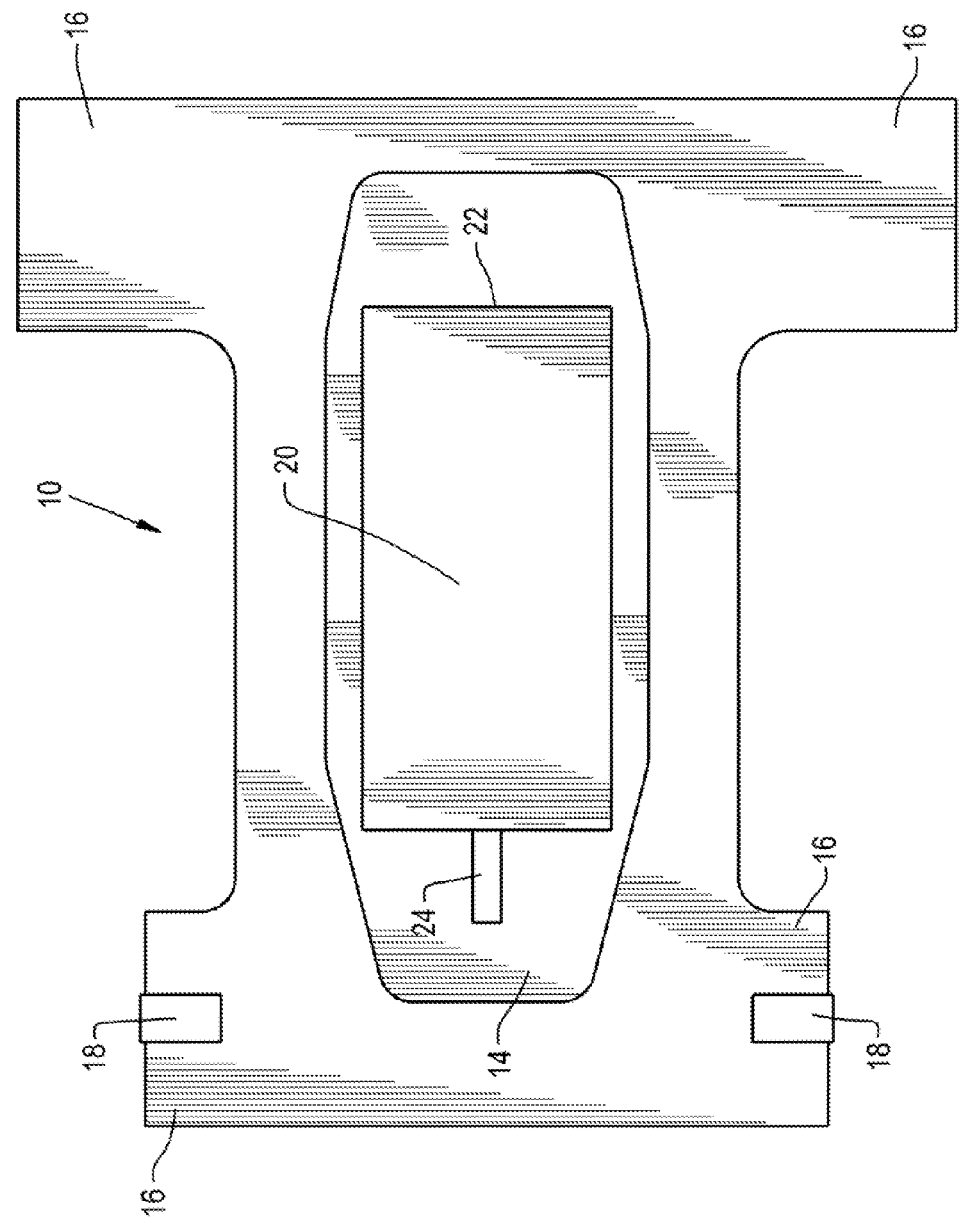
FIG. 2 represents an open top view of a medicated diaper in accordance with certain aspects of this invention.
Figure 3:
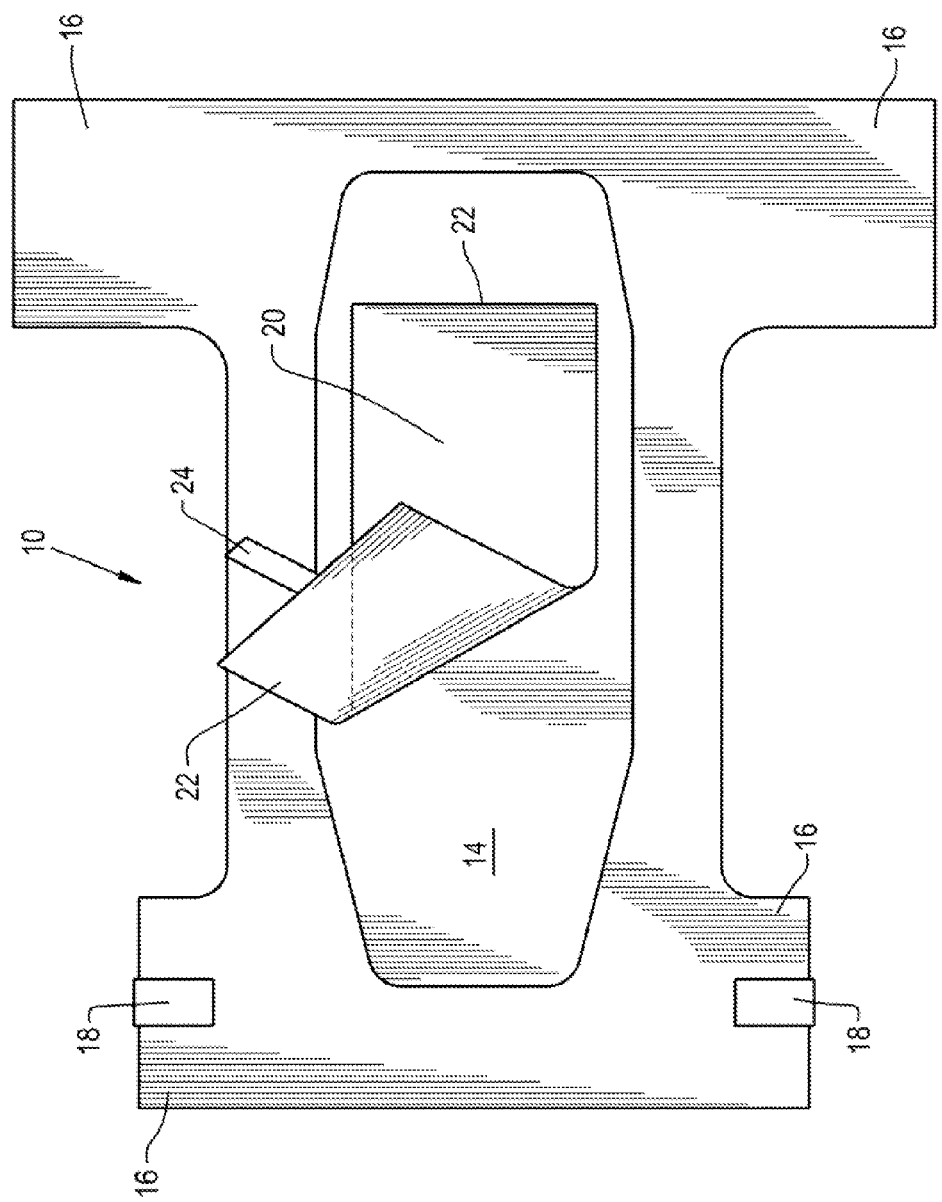
FIG. 3 represents a cover being removed from a medicated diaper in accordance with certain aspects of this invention.

According to a preferred aspect of the invention, the diaper 10 further includes one or more compositions or medications, for example, a cream, lotion, ointment, liquid, etc., located on and/or within a medicated area 20 of the diaper 10 such that, during use of the diaper 10 by an individual, the medication may contact an area of the individual that is at risk of forming a skin rash due to prolonged use of the diaper 10. The medicated area 10 may be of any size, shape, or medication concentration suitable for reducing the likelihood of skin rashes and/or pressure ulcers. FIGS. 1B, 2, and 3 generally represent the medicated area 20 as being located near a central region of the absorption area 14; however, it is foreseeable and within the scope of the invention that the medicated area 20 may be located elsewhere on the diaper 10, or could encompass a majority or the entirety of an interior of the diaper 10. For example, the medicated area 20 may include an entirety of the interior portions of the absorption area 14 and the flaps 16. While the figures represent the diaper 10 as including a single medicated area 20, it is also within the scope of the invention that the diaper 10 includes any number of medicated areas 20, and such medicated areas 20 could individually be of any size, shape, or medication concentration. According to one nonlimiting example, the medicated area 20 is located at a central region of the absorption area 14 and extends to oppositely disposed sides of the absorption area 14 and extends about three inches from the center of the absorption area 14 towards both the front and rear ends of the diaper 10. The medicated area 20 may be formed of the same material or combination of materials as the absorption area 14, or may comprise entirely different materials. Regardless, the medicated area 20 preferably performs liquid absorption in addition to carrying or bearing the medication. Preferably, the medication is at least partially located on or at an outermost surface of the interior of the diaper so as to directly contact the skin of the user when the diaper is being worn.

Prior to use by an individual, the medicated area 20 may be sealed or covered by a cover 22 suitable for reducing loss of the medication from the diaper 10 due to physical contact, evaporation, or other means of loss. Preferably, the cover 22 is adapted to be readily removed from the diaper 10 prior to use. For example, the cover 22 may be secured to the diaper 10 with a securing agent such as a glue or tape, or with perforated edges along its perimeter, or be removably secured to the diaper 10 by any other means known in the art. For example, the cover 22 may be formed of a thin polymer film similar to those used for sealing food items which may cling to the medicated area 20 for a variety of reasons such as due to moisture in the medicated area 20 or due to the inherent physical properties of the film itself. Such films are generally formed of vinyl, polyvinyl chloride, or low density polyethylene. However, the cover 22 may be formed of any material suitable for reducing loss of the medication from the diaper 10, preferably by forming a moisture seal over the medicated area 20.

A tab 24 may optionally be provided to facilitate removal of the cover 22 from the diaper 10. The tab 24 may be formed as a integral portion of the cover 22 or may be a separate component secured to the cover 22. With the tab 24, an individual may pull the tab 24 in a direction from one side or end towards the opposite side or end of the diaper 10 in order to, for example, dislodge the securing agent, tear the perforated edges, or otherwise release the means by which the cover 22 is secured to the medicated area 20 and thereby partially or, preferably, entirely remove the cover 22 from of the diaper 10. Although the tab 24 is represented in the figures as comprising an elongated rectangular body, the tab 24 may be of any size or shape, and may be located anywhere on the cover 22. For example, the cover 22 may be secured to the medicated area 20 with a securing agent and the tab 24 may comprise a corner of the cover 22 on which the securing agent is absent. Removal of the cover 22 preferably exposes the medicated area 20 such that once the diaper 10 is secured to an individual, the medication of the medicated area 20 contacts an area of the individual that is at risk of forming a skin rash due to prolonged use of the diaper 10, or at risk of forming a pressure ulcer due to extended periods of pressure applied to the area. Preferably, the cover 22 is configured to be entirely removed from the diaper 10 without leaving behind any remaining perforations, rough areas, or other structures that could cause irritation to skin.

The medication may be of any composition and concentration suitable for reducing or preventing the risk of skin rash and/or pressure ulcer formation during use of the diaper 10 according to convention wear time periods. For example, the medication may comprise a composition similar to those known in the art of consumer and medical products suitable for protecting skin, preferably by reducing one or more of heat, moisture, and friction on or near the skin. Such medications may reduce the formation of blanching of the skin due to long periods of sitting or lying on bony prominences or other potential pressure points for extended amounts of time or extended wear of the diaper 10. An exemplary composition of the medication includes a skin protectant commercially available under the trademark Nutrashield® produced by Medline under the Remedy® product line. Investigations leading to the present invention found particular success with skin protectant products commercially available under the trademark Desitin® produced by Johnson & Johnson Consumer Inc. Preferably, the medicated area 20 includes an amount and concentration of the medication which is equal to or more than a recommended amount and concentration as described by the product instructions for conventional recommended use.

In a first investigation leading to the present invention, various different medications were applied to absorption areas 14 of various different brands of diapers to define medicated areas 20 thereon. These medicated areas were then sealed with covers 22 formed of thin polymeric films. The medicated areas 20 were thereafter checked at intervals over a period of time. It was observed that the medications of the medicated areas 20 remained suitably moist for time periods in excess of six months, indicating that medicated diapers 10 can be manufactured to have a reasonable usable shelf life. In contrast, it has been observed that when a medication is applied to a conventional diaper without the cover 22, the medication generally dries, evaporates, or otherwise becomes unuseable, under some circumstances within about four to eight hours.

Medicated diapers 10 as described herein provide constant protection to an individual's skin during use of the diaper 10. By providing a medication on the medicated area 20 of the diaper 10 that will contact the individual's skin during use, the formation of skin rashes and/or pressure ulcers can be significantly reduced or eliminated. Furthermore, by manufacturing the medicated diapers 10 with the medicated area 20 thereon, there is either no need or a reduced need for an individual or caregiver to apply a medication, for example, a cream, lotion, ointment, powder, etc., to the individual's skin or the diaper prior to use of the diaper. This not only can simplify the diaper changing process, but further controls the amount and concentration of the medication used on an individual. Relative to conventional methods of applying medications to the skin or diaper of an individual by hand, the medicated diaper 10 allows for both a reduction of waste which could result from the application of excess amounts of the medication and the reduction in a likelihood of skin rash or pressure ulcer formation which could result from the application of an inadequate amount of the medication.

While the invention has been described in terms of specific embodiments, it is apparent that other forms could be adopted by one skilled in the art. For example, the physical configuration of the medicated diaper 10 could differ from that shown, and materials and processes/methods other than those noted could be used. Therefore, the scope of the invention is to be limited only by the following claims.

The invention claimed is:

1. A diaper comprising:
an interior forming an outermost surface of the diaper that directly contacts skin of an individual when the individual is wearing the diaper, the interior comprising an absorption area adapted for absorbing urine;
a layer of a medication on top of and coating the outermost surface of the interior at the absorption area so as to define a medication area as a continuous surface region on the outermost surface so that the medication area directly contacts the skin of the individual when the individual is wearing the diaper, the medication containing moisture and being formulated to reduce risk of formation of a rash or pressure ulcer on the skin of the individual; and
a cover removably secured to the medication area solely by clinging to the medication area due to the moisture in the medication to provide a moisture seal over the medication area, and preventing loss of the medication prior to removal of the cover.

2. The diaper of claim 1, wherein the cover is a polymer film.

3. The diaper of claim 2, wherein the polymer film is a vinyl, polyvinyl chloride, or low density polyethylene.

4. The diaper of claim 1, further comprising a tab at an end of the cover and configured to facilitate removal of the cover from the diaper to expose the medication.

5. A method of using the diaper of claim 1, the method comprising removing the cover to expose the medication, and then securing the diaper to an individual so that the medication directly contacts the skin of the individual without first applying a composition to the skin of the individual or the diaper.

6. A method of manufacturing a diaper adapted to prevent or reduce the risk of the formation of a rash or a pressure ulcer on skin of an individual due to the individual wearing the diaper over an extended period, the method comprising:
manufacturing the diaper to have an interior forming an outermost surface of the diaper that directly contacts the skin of the individual when the individual is wearing the diaper, the interior comprising an absorption area adapted for absorbing urine;
providing a layer of a medication on top of and coating the outermost surface of the interior at the absorption area so as to define a medication area as a continuous surface region on the outermost surface so that the medication area directly contacts the skin of the individual when the individual is wearing the diaper, the medication containing moisture;
applying a removable cover over the medication area so that the removable cover is removably secured to the medication area solely by clinging to the medication area due to the moisture in the medication to provide a moisture seal over the medication area that conceals and seals the medication to prevent loss of the medication prior to the individual wearing the diaper; and
offering the diaper for purchase.

7. The method of claim 6, further comprising securing a tab at an end or side of the removable cover, the tab being configured to facilitate removal of the removable cover from the diaper to expose the area comprising the composition.

8. The method of claim 6, wherein the removable cover is a polymer film.

9. The method of claim 8, wherein the polymer film is a vinyl, polyvinyl chloride, or low density polyethylene.

* * * * *